(12) United States Patent
Terazaki

(10) Patent No.: US 8,173,111 B2
(45) Date of Patent: *May 8, 2012

(54) HAIR CLEANSING COMPOSITIONS

(75) Inventor: Hiroyuki Terazaki, Tokyo (JP)

(73) Assignee: Kao Corporation, Tokyo (JP)

( * ) Notice: Subject to any disclaimer, the term of this patent is extended or adjusted under 35 U.S.C. 154(b) by 1477 days.

This patent is subject to a terminal disclaimer.

(21) Appl. No.: 10/375,032

(22) Filed: Feb. 28, 2003

(65) Prior Publication Data

US 2003/0185783 A1 Oct. 2, 2003

(30) Foreign Application Priority Data

Mar. 1, 2002 (JP) ................................ 2002-055884

(51) Int. Cl.
*A61Q 5/02* (2006.01)

(52) U.S. Cl. ................ 424/70.19; 424/70.24; 424/70.11

(58) Field of Classification Search ........................ None
See application file for complete search history.

(56) References Cited

U.S. PATENT DOCUMENTS

| | | | | |
|---|---|---|---|---|
| 5,403,517 A | * | 4/1995 | Horinishi et al. | 424/70.21 |
| 5,683,685 A | * | 11/1997 | Hirano et al. | 424/78.03 |
| 5,785,962 A | | 7/1998 | Hinz et al. | |
| 6,099,828 A | * | 8/2000 | Kajino et al. | 424/70.15 |
| 6,231,843 B1 | | 5/2001 | Hoelzel et al. | |
| 6,730,292 B1 | * | 5/2004 | Yang et al. | 424/70.11 |
| 6,746,492 B2 | * | 6/2004 | Kawai et al. | 8/405 |
| 6,914,038 B2 | * | 7/2005 | Terazaki et al. | 510/122 |
| 6,979,439 B1 | * | 12/2005 | Sakai et al. | 424/70.8 |
| 2002/0037266 A1 | * | 3/2002 | Terazaki et al. | 424/70.12 |
| 2003/0147824 A1 | * | 8/2003 | Terazaki et al. | 424/70.2 |
| 2003/0170197 A1 | * | 9/2003 | Terazaki et al. | 424/70.24 |

FOREIGN PATENT DOCUMENTS

| | | |
|---|---|---|
| DE | 10200185 | * 7/2002 |
| EP | 0 403 304 | 12/1990 |
| EP | 0 855 178 | 7/1998 |
| EP | 0 978 272 | 2/2000 |
| EP | 1 016 401 | 7/2000 |
| JP | 2000-327540 | 11/2000 |
| JP | 2002-29940 | 1/2002 |
| JP | 2003-2810 | 1/2003 |
| JP | 2003-40724 | 2/2003 |
| WO | WO 92/21320 | 12/1992 |

OTHER PUBLICATIONS

Patent Abstracts of Japan, JP 2000-327540, Nov. 28, 2000.
U.S. Appl. No. 10/375,037, filed Feb. 28, 2003, Terazaki.
Helioff, M. W., et al., "Shampoo Innovation Via a New Surfactant," Drug & Cosmetic Industry, 142(4), 1988, pp. 38-42, XP009086241.

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

A hair cleansing composition comprises the following ingredients (A) to (C):
(A) a hydroxymonocarboxylic acid, or a salt thereof,
(B) an organic solvent, and
(C) an anionic surfactant having a sulfate group; and has a pH of from 1 to 4 when diluted 20-fold by weight with water and a buffer capacity not lower than 0.005 gram equivalent/L but lower than 0.2 gram equivalent/L.

15 Claims, No Drawings

HAIR CLEANSING COMPOSITIONS

TECHNICAL FIELD

This invention relates to hair cleansing compositions, which have a good foamability and a highly lubricious foam quality during washing, and are excellent in the luster, softness and manageability of hair after drying and also superb in stability.

BACKGROUND ART

In hair treatments such as hair rinses and hair conditioners, it is practiced to lower the pH of their systems to impart luster and softness to hair. No attempt has, however, been made to lower the pH of hair cleansing compositions, because the hair cleansing compositions are intended to impart neither luster nor softness in general.

With a view to providing hair cleansing compositions with functions to give such luster, softness and manageability as described above, the present inventors conducted research on low-pH hair cleansing compositions which made use of organic acids. A problem, however, arose in that in a low pH range, anionic surfactants as cleansing ingredients underwent decomposition, resulting in stability deterioration such as gelling of systems and reduction in foamability. On the other hand, hair itself has a buffer capacity. A simple application of a treatment to hair, therefore, leads to a change in the pH of the treatment solution, raising a problem that its intended effects cannot be fully brought about.

DISCLOSURE OF THE INVENTION

The object of the present invention is to provide a hair cleansing composition, which is excellent in stability, can effectively impart luster, softness and manageability to hair, and has a good foamability and a highly lubricious foam quality during washing.

The present inventors have found that impartment of a buffer capacity to a hair cleansing composition can inhibit decomposition of an anionic surfactant in a low pH range and can also reduce a change in pH during hair washing, and as a result, that a hair cleansing composition capable of meeting the above-described requirements can be obtained.

Specifically, the present invention provides a hair cleansing composition comprising the following ingredients (A) to (C):
(A) a hydroxymonocarboxylic acid or a salt thereof,
(B) an organic solvent selected from the following organic solvents (b1) to (b5):
  (b1) a compound represented by the following formula (1):

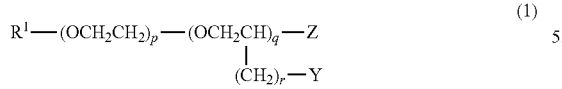

wherein $R^1$ represents a hydrogen atom or a lower alkyl group, Y and Z each independently represents a hydrogen atom or a hydroxyl group, and p, q and r each independently denotes an integer of from 0 to 5, with a proviso that, when p=q=0, both Z and $R^1$ are not a hydrogen atom,
  (b2) an N-alkylenepyrrolidone with an alkyl group having 1 to 18 carbon atoms attached to the nitrogen atom,
  (b3) an alkylene carbonate having 1 to 4 carbon atoms,
  (b4) a polypropylene glycol having a molecular weight of from 200 to 5,000, and
  (b5) a lactone or cyclic ketone represented by the following formula (2), (3) or (4):

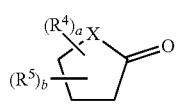

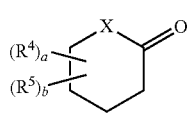

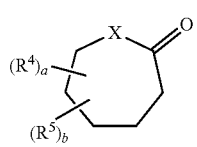

wherein X represents a methylene group or an oxygen atom, $R^4$ and $R^5$ represent different substituent groups and a and b each independently represents 0 or 1, and
(C) an anionic surfactant having a sulfate group;
wherein the hair cleansing composition has a pH of from 1 to 4 when diluted 20-fold by weight with water, and also a buffer capacity not lower than 0.005 gram equivalent/L but lower than 0.2 gram equivalent/L.

Owing to the above-described features, the hair cleansing composition according to the present invention has a good foaming ability and a highly lubricious foam quality during washing and is excellent in the luster, softness and manageability of hair after drying and also superb in stability.

BEST MODES FOR CARRYING OUT THE INVENTION

Examples of the hydroxymonocarboxylic acid as the ingredient (A) can include glycolic acid, lactic acid, hydroxyacrylic acid, oxybutyric acid, and glycerin, with lactic acid and glycolic acid being particularly preferred. Examples of the salt of the hydroxymonocarboxylic acid can include its sodium salt, potassium salt and ammonium salt.

Two or more of these hydroxymonocarboxylic acids and salts thereof may be used in combination as the ingredient (A). From the standpoint of improvements in the finish of hair such as luster and style, the content of the ingredient (A) may range preferably from 0.05 to 10 wt. %, more preferably from 0.1 to 5 wt. %, particularly from 0.5 to 2 wt. % in terms of free acid, all based on the hair cleansing composition according to the present invention.

Among the organic solvents as the ingredient (B), illustrative of the compound (b1) are ethanol, 1-propanol, 2-propanol, butanol, isobutanol, ethylene glycol, propylene glycol, 1,3-butanediol, methyl carbitol, ethyl carbitol, propyl carbitol, butyl carbitol, triethylene glycol monoethyl ether, triethylene glycol monobutyl ether, and glycerin. Illustrative of the N-alkylpyrrolidone (b2) are N-methylpyrrolidone, N-octylpyrrolidone, and N-laurylpyrrolidone. Illustrative of the alkylene carbonate (b3) are ethylene carbonate and propylene carbonate. Preferred examples of the polypropylene glycol (b4) can include those having molecular weights of from 200 to 1,000, especially those having molecular weights of from 300 to 400. In the lactone or cyclic ketone (b5), $R^4$ and $R^5$ in the formulas (2) to (4) may each preferably be a linear, branched or cyclic alkyl group, a hydroxyl group, a sulfonic acid group, a phosphoric acid group, a carboxyl group, a phenyl group, a sulfoalkyl group, an alkyl phosphate group, a carboxyalkyl group, or the like. In the case where the compound (b5) is γ-lactone or δ-lactone, $R^4$ and $R^5$ may preferably be linear or branched alkyl groups having 1 to 6 carbon atoms, for example, methyl groups, ethyl groups, propyl groups, isopropyl groups or butyl groups substituted at the γ or δ positions, in other words, at the methylene groups adjacent to the oxygen heteroatom. When it is desired to increase the water solubility of the compounds (2) to (4), they preferably contain as $R^4$ or $R^5$ an acidic group such as a sulfonic acid group, phosphoric acid group or carboxyl group or an alkyl group substituted with one or more of such acidic groups. Examples of the lactone (b5) include γ-butyrolactone, γ-caprolactone, γ-valerolactone, δ-valerolactone, δ-caprolactone, and δ-heptanolactone. From the standpoint of the stability of the lactone, γ-lactones, especially γ-butyrolactone and γ-caprolactone are preferred. Examples of the cyclic ketone (b5) can include cyclopentanone, cyclohexanone, cycloheptanone, and 4-methylcycloheptanone.

Two or more of these organic solvents may be used in combination as the ingredient (B). From the standpoint of improvements in use feeling, luster and softness, the content of the ingredient (B) may range preferably from 0.01 to 50 wt. %, more preferably from 0.1 to 35 wt. %, particularly from 0.5 to 10 wt. %, all based on the hair cleansing composition according to the present invention.

Examples of the sulfate-type anionic surfactant as the ingredient (C) can include polyoxyethylene alkyl ether sulfates, polyoxyethylene alkenyl ether sulfates, alkyl sulfates, and polyoxyalkylene alkyl phenyl ether sulfates. Particularly preferred are those represented by the following formula (5) or (6):

$$R^6O(CH_2CH_2O)_mSO_3M \quad (5)$$

$$R^7OSO_3M \quad (6)$$

wherein $R^6$ represents an alkyl group or alkenyl group having 10 to 18 carbon atoms, $R^7$ represents an alkyl group having 10 to 18 carbon atoms, M represents an alkali metal, alkaline earth metal, ammonium, alkanolamine or basic amino acid, and m stands for a number of from 1 to 5.

Two or more of these sulfates may be used in combination as the ingredient (C). From the standpoint of foamability and also of liquid properties and cleansing property at the time of use, the content of the ingredient (C) may range preferably from 1 to 50 wt. %, more preferably from 8 to 30 wt. %, particularly from 10 to 22 wt. %, all based on the hair cleansing composition according to the present invention.

To improve the finish after drying, one or more conditioning ingredients selected from cationic polymers, cationic surfactants, silicones and oils may be incorporated further in the hair cleansing composition according to the present invention.

Examples of the cationic polymers include cationic cellulose derivatives, cationic starch, cationic guar gum derivatives, homopolymers of diallyl quaternary ammonium salt, diallyl quaternary ammonium salt/acrylamide copolymers, quaternized polyvinyl-pyrrolidone derivatives, polyglycol polyamine condensation products, vinylimidazolium trichloride/vinylpyrrolidone copolymers, hydroxyethylcellulose/dimethyldiallylammonium chloride copolymers, vinylpyrrolidone/quaternized dimethylaminoethyl methacrylate copolymers, polyvinylpyrrolidone/alkyl aminoacrylate copolymers, polyvinylpyrrolidone/alkyl aminoacrylate/vinyl caprolactam copolymers, vinylpyrrolidone/methacrylamidopropyl trimethylammonium chloride copolymers, alkylacrylamide/acrylate/alkylaminoalkylacrylamide/polyethylene glycol methacrylate copolymers, adipic acid/dimethylaminohydroxypropyl ethylenetriamine copolymers ("Cartaretin"; product of Sandoz Chemicals Corp., U.S.A.), and cationic polymers disclosed in JP-A-53139734 and JP-A-60036407. Particularly preferred are cationic cellulose derivatives and cationic guar gum derivatives.

Example of the cationic surfactants can include lauryltrimethylammonium chloride, cetyltrimethylammonium chloride, cetyltrimethylammonium bromide, stearyltrimethylammonium chloride, stearyltrimethylammonium bromide, lauryltrimethylammonium bromide, dialkyldimethylammonium chlorides, dicetyldimethylammonium chloride, distearyldimethylammonium chloride, dicocoyldimethylammoium chloride, myristyldimethylbenzylammnoium chloride, stearyldimethylbenzylammonium chloride, lanolin fatty acid aminopropylethyldimethylammonium ethyl sulfate, lanolin fatty acid aminoethyltriethylammonium ethyl sulfate, stearylamidopropyldimethylamine (and its salts), stearylamidoethyldiethylamine (and its salts), lanolin fatty acid aminopropyltriethylammonium ethyl sulfate, lanolin fatty acid aminoethyltrimethylammonium methyl sulfate, lanolin fatty acid aminopropylethyldimethylammonium methyl sulfate, isoalkanoic acid ($C_{14}$-$C_{20}$) aminopropylethyldimethylammonium ethyl sulfate, isoalkanoic acid ($C_{18}$-$C_{22}$) aminopropylethyldimethylammonium ethyl sulfate, isostearic acid aminopropylethyldimethylammonium ethyl sulfate, isononanoic acid aminopropylethyldimethyl ammonium ethyl sulfate, and alkyltrimethylammonium saccharins.

Examples of the silicones can include the followings:
(Silicones-1) Dimethylpolysiloxanes
Illustrative are those represented by the following formula:

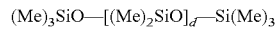

$$(Me)_3SiO\text{---}[(Me)_2SiO]_d\text{---}Si(Me)_3$$

wherein each Me represents a methyl group, and d stands for a number of from 3 to 20,000.
(Silicones-2) Amino-Modified Silicones
One having an average molecular weight of from about 3,000 to 100,000 and listed under the name of "Amodimethicone" in the third edition of the CTFA dictionary (Cosmetic Ingredient Dictionary, U.S.A.) is preferred, although a variety of amino-modified silicones are usable. This amino-modified silicone can be used preferably as an aqueous emulsion, and its commercial products include "SM 8704C" (Dow Corning-Toray-Silicone Co., Ltd.) and "DC 929" (Dow Corning Corporation).
(Silicones-3) Other Silicones
As silicones other than those described above, there are also polyether-modified silicones, methylphenylpolysiloxane, fatty acid-modified silicones, alcohol-modified silicones, alkoxy-modified silicones, epoxy-modified silicones, fluorine-modified silicones, cyclic silicones, alkyl-modified silicones, and the like.

The term "oils" as used herein means oils other than silicones. Illustrative are hydrocarbons such as squalene, squalane, liquid paraffin, and cycloparaffin; glycerides such as castor oil, cacao oil, mink oil, avocado oil, and olive oil; waxes such as beeswax, whale wax, lanolin, and carnauba wax; alcohols such as cetyl alcohol, oleyl alcohol, stearyl alcohol, isostearyl alcohol, 2-octyldodecanol, and glycerin; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acids, isostearic acid, and isopalmitic acid; isostearyl glyceryl ethers; and polyoxypropylene butyl ether. Of these, esters are preferred, with hexadecyl 2-ethylhexanoate, isononyl isononanoate and isopropyl palmitate are particularly preferred.

Two or more of these conditioning ingredients may be used in combination. From the standpoint of foam lubricity and also of smoothness from washing to rinsing, the content of the conditioning ingredient may range preferably from 0.05 to 10 wt. %, more preferably from 0.1 to 5 wt. %, particularly preferably from 0.3 to 2 wt. %, all based on the hair cleansing composition according to the present invention.

To further improve the foam performance of the hair cleansing composition according to the present invention, one or more surfactants selected from anionic surfactants other than the ingredient (C), nonionic surfactants and amphoteric surfactants may also be incorporated.

The anionic surfactants other than the ingredient (C) can include sulfonate-type anionic surfactants and carboxylate-type anionic surfactants. Illustrative are alkyl sulfosuccinate salts, alkyl polyoxyalkylene sulfosuccinate salts, higher fatty acid salts, and alkanesulfonate salts.

Examples of the nonionic surfactants can include polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglyceryl alkyl ethers, polyglyceryl fatty acid esters, fatty acid alkanolamides, and alkyl glycosides. Among these, alkyl glycosides, polyoxyalkylene ($C_8$-$C_{20}$) fatty acid esters, polyoxyethylene sorbitan fatty acid esters, polyoxyethylene hydrogenated castor oil and fatty acid alkanolamides are preferred. Preferred fatty acid alkanolamides are those containing acyl groups having the carbon numbers of from 8 to 18, especially from 10 to 16. The fatty acid alkanolamides can be either monoalkanolamides or dialkanolamides. Preferred are those containing hydroxyalkyl groups having the carbon numbers of from 2 to 3. Illustrative are oleic acid diethanolamide, palm kernel oil fatty acid diethanolamide, coconut oil fatty acid diethanolamide, lauric acid diethanolamide, polyoxyethylene coconut oil fatty acid monoethanolamides, coconut oil fatty acid monoethanolamides, lauric acid isopropanolamide, and lauric acid monoethanolamide.

The amphoteric surfactants can include betaine-type surfactants. Among these, betaine-type surfactants such as alkyldimethylaminoacetic acid betaines and fatty acid amidopropyl betaines are more preferred, with fatty acid amidopropyl betaines being particularly preferred. Of these fatty acid amidopropyl betaines, preferred are those having acyl groups whose carbon numbers are from 8 to 18, especially from 10 to 16. Particularly preferred are lauric acid amidopropyl betaine, palm kernel oil fatty acid amidopropyl betaines, and coconut oil fatty acid amidopropyl betaines.

In addition to the above-described ingredients, ingredients which are employed in ordinary hair cleansing compositions can also be incorporated in the hair cleansing composition according to the present invention as needed depending upon the purpose of use. Such ingredients can include, for example, antidandruff agents; vitamins; anti-inflammatories; preservatives; chelating agents; humectants such as sorbitol and panthenol; colorants such as dyes and pigments; viscosity controlling agents such as hydroxyethylcellulose, methylcellulose, polyethylene glycol, and clay mineral; pH adjusters such as potassium hydroxide; plant extracts; pearlants; fragrances; color additives; ultraviolet absorbers; antioxidants; and ingredients described in ENCYCLOPEDIA OF SHAMPOO INGREDIENTS (MICELLE PRESS).

From the viewpoint of imparting luster and softness to hair and also reducing irritation, the hair cleansing composition according to the present invention has a pH of from 1 to 4, preferably from 2 to 4, particularly preferably from 3 to 3.9 when diluted 20-fold by weight with water (to the concentration upon application to hair).

From the standpoint of inhibiting decomposition of the ingredient (C) and also decreasing changes in pH during hair cleaning, the hair cleansing composition according to the present invention is required to have a buffer capacity not lower than 0.005 gram equivalent/L but lower than 0.2 gram equivalent/L, preferably not lower than 0.01 gram equivalent/L but lower than 0.2 gram equivalent/L, more preferably not lower than 0.015 gram equivalent/L but lower than 0.2 gram equivalent/L when diluted 20-fold by weight with water. The term "buffer capacity" as used herein means a value determined by the following equation while using as a measure the concentration of a base required to raise the pH of the 20-fold dilute aqueous solution at 25° C. by 1 from its initial value.

$$\text{Buffer capacity} = |dC_B/dpH|$$

wherein $C_B$ represents an ion concentration (gram equivalent/L) of the base.

Such a buffer capacity can be imparted by adding a pH buffering agent or the like to the hair cleansing composition. Usable as the pH buffering agent is an organic acid or inorganic acid or a salt thereof, which exhibits a buffering action in a pH range of from 1 to 4. Examples of the organic acid can include, in addition to the ingredient (A), citric acid, succinic acid, tartaric acid, fumaric acid, malic acid, levulinic acid, butyric acid, valeric acid, oxalic acid, maleic acid and mandelic acid. Examples of the inorganic acid can include phosphoric acid, sulfuric acid, and nitric acid. Further, examples of the salt of such an acid can include its alkali metal salts such as the sodium salt and the potassium salt; its ammonium salt; and its alkanolamine salts such as the triethanolamine salt. No particular limitation is imposed on the amount of the pH buffering agent to be added, and its amount varies depending on the kind of the compound giving buffering ability. When sodium citrate is used as a primary compound giving the buffering ability, for example, it can be added at a concentration of about 1 wt. % or higher.

The form of the hair cleansing composition according to the present invention can be chosen as desired, from a liquid form, a powder form, a gel form, a granular form, etc. However, a liquid form making use of water or a lower alcohol as a solvent, especially water, is preferred.

The hair cleansing composition according to the present invention can be formulated into a product for use in a bathroom such as a shampoo composition, a shampoo with rinse, a treatment or a conditioner, especially a shampoo composition.

EXAMPLES

In the following Examples and Comparative Examples, "pH" indicates a pH of a hair composition diluted 20-fold by weight with water.

Examples 1-4 and Comparative Examples 1-4

Shampoo compositions shown in Table 1 were prepared, and their organoleptic ranking was conducted.

(Washing Method)

Subsequent to thorough moistening of hair, 5 g or 10 g (5 g for semi-long hair, 10 g for long hair) of a shampoo composition were dispensed, and then, the hair was washed with the composition. The hair was rinsed thoroughly and then dried fully with hot air from a dryer.

(Organoleptic Evaluation)

Evaluation was conducted by five expert panelists in accordance with the following ranking criterion, and based on average scores, the shampoo compositions were ranked.

Ranking criterion
- (1) Luster of hair after drying
    - 4: Pronounced improvement in luster is observed.
    - 3: Improvement in luster is observed.
    - 2: Some improvement in luster is observed.
    - 1: No improvement in luster.
    - 0: Luster is lost.
- (2) Softness of hair after drying
    - 4: Very soft.
    - 3: Soft.
    - 2: Slightly soft.
    - 1: Not soft.
    - 0: Not soft at all.
- (3) Manageability of hair after drying
    - 4: Very good manageability.
    - 3: Good manageability.
    - 2: Average manageability.
    - 1: Somewhat poor manageability.
    - 0: No manageability.

Ranking
- A: Average ranking score $\geq 3.5$
- B: $3.5 >$ Average ranking score $\geq 2.5$
- C: $2.5 >$ Average ranking score $\geq 1.5$
- D: $1.5 >$ Average ranking score Example 5

Clear Shampoo

| | (wt. %) |
|---|---|
| Sodium POE(2) lauryl ether sulfate | 10.0 |
| Cationic guar gum | 0.1 |
| Lactic acid | 0.75 |
| Sodium chloride | 1.0 |
| Lauroylamidopropyl betaine | 1.0 |
| Cocoyl monoethanolamide | 0.3 |
| Propylene carbonate | 0.5 |
| Glycerin | 1.0 |
| Sodium hydroxide | q.s. to pH 4 |
| Deionized water | Balance |

The above-described shampoo (pH: 4.0, buffer capacity: 0.008) was excellent in foaming property and foam lubricity during washing, smoothness during rinsing, and hair luster and softness after drying, and was also superb in stability.

Example 6

Conditioning Shampoo

| | (wt. %) |
|---|---|
| Sodium POE(2) lauryl ether sulfate | 8.0 |
| Cationic guar gum | 0.5 |
| Glycolic acid | 0.75 |
| Disodium citrate | 1.0 |
| Lauroylamidopropyl betaine | 3.0 |
| Cocoyl monoethanolamide | 0.7 |
| Myristyl alcohol | 1.0 |

TABLE 1

| | Ingredients (wt. %) | Examples | | | | Comparative Examples | | | |
|---|---|---|---|---|---|---|---|---|---|
| | | 1 | 2 | 3 | 4 | 1 | 2 | 3 | 4 |
| (A) | Glycolic acid | 2 | — | — | — | — | — | — | — |
| | Lactic acid | — | 2 | 2 | 2 | — | — | — | 0.05 |
| (B) | Polypropylene glycol (Mw = 400) | 1 | — | — | 0.5 | 1 | — | — | — |
| | Propylene carbonate | — | 1 | — | — | — | — | — | — |
| | N-methylpyrrolidone | — | — | 0.5 | — | — | 0.5 | — | — |
| (C) | Sodium POE(2) lauryl ether sulfate | 10 | 10 | 10 | 10 | 10 | 10 | 10 | 10 |
| | Sodium lauryl sulfate | 5 | 5 | 5 | 5 | 5 | 5 | 5 | 5 |
| Others | Myristyl alcohol | 1 | 1 | 1 | 1 | 1 | 1 | 1 | 1 |
| | Cocoyl monoethanolamide | 0.5 | 0.5 | 0.5 | 0.5 | 0.5 | 0.5 | 0.5 | 0.5 |
| | Ethylene glycol distearate | 1 | 1 | 1 | 1 | 1 | 1 | 1 | 1 |
| | Cationic hydroxyethylcellulose | 0.3 | 0.3 | 0.3 | 0.3 | 0.3 | 0.3 | 0.3 | 0.3 |
| | Cationic guar gum | 0.5 | 0.5 | 0.5 | 0.5 | 0.5 | 0.5 | 0.5 | 0.5 |
| | NaOH Aqueous solution | q.s.* | q.s.* | q.s.* | q.s.* | q.s.* | q.s.* | q.s.* | q.s.* |
| | Purified water | Bal. | Bal. | Bal. | Bal. | Bal. | Bal. | Bal. | Bal. |
| pH (when diluted 20-fold by weight) | | 3.5 | 3.5 | 3.5 | 3.5 | 3.5 | 3.5 | 3.5 | 5.0 |
| Buffer capacity (NaOH-gram equivalent/L) | | 0.02 | 0.01 | 0.01 | 0.01 | 0.003 | 0.003 | 0.003 | 0.002 |
| Ranking | Luster of hair | A | A | A | A | C | B | B | B |
| | Manageability of hair | A | A | A | A | B | C | B | B |
| | Softness of hair | A | A | A | A | C | C | C | C |

*Amount sufficient to adjust the pH.

-continued

|  | (wt. %) |
| --- | --- |
| Ethylene glycol distearate | 3.0 |
| Polypropylene glycol (Mw = 400) | 0.5 |
| Glycerin | 1.0 |
| Deionized water | Balance |

The above-described shampoo (pH: 3.5, buffer capacity: 0.01) was excellent in foaming property and foam lubricity during washing, smoothness during rinsing, and hair luster and softness after drying, and was also superb in stability.

Example 7

Conditioning Shampoo

|  | (wt. %) |
| --- | --- |
| Sodium POE(2) lauryl ether sulfate | 11.0 |
| Sodium lauryl sulfate | 5.0 |
| Cationic guar gum | 0.3 |
| Malic acid | 0.1 |
| Lactic acid | 0.75 |
| Sodium chloride | 0.2 |
| N-methylpyrrolidone | 0.2 |
| Propylene carbonate | 0.3 |
| Cocoyl monoethanolamide | 1.0 |
| Dimethicone (viscosity: 100,000 mPa · s) | 0.5 |
| Amodimethicone | 0.1 |
| Myristyl alcohol | 1.0 |
| Cetanol | 0.5 |
| Ethylene glycol distearate | 3.0 |
| Cationic hydroxyethylcellulose | 0.3 |
| Glycerin | 1.0 |
| Sodium hydroxide | q.s. to pH 3.7 |
| Deionized water | Balance |

The above-described shampoo (pH: 3.7, buffer capacity: 0.009) was excellent in foaming property and foam lubricity during washing, smoothness during rinsing, and hair luster and softness after drying, and was also superb in stability.

Example 8

Conditioning Shampoo

|  | (wt. %) |
| --- | --- |
| Sodium POE(2) lauryl ether sulfate | 8.0 |
| Cationic guar gum | 0.3 |
| Malic acid | 0.3 |
| Lactic acid | 1.0 |
| Sodium chloride | 1.0 |
| Lauroylamidopropyl betaine | 3.0 |
| Myristyl alcohol | 1.0 |
| Cetanol | 0.5 |
| Behenyltrimonium chloride | 0.5 |
| Ethylene glycol distearate | 2.0 |
| γ-Butyrolactone | 0.1 |
| Polypropylene glycol (m.w. 400) | 0.4 |
| Sodium hydroxide | q.s. to pH 3.9 |
| Deionized water | Balance |

The above-described shampoo (pH: 3.9, buffer capacity: 0.008) was excellent in foaming property and foam lubricity during washing, smoothness during rinsing, and hair luster and softness after drying, and was also superb in stability.

Example 9

Antidandruff Shampoo

|  | (wt. %) |
| --- | --- |
| Sodium POE(2) lauryl ether sulfate | 10.0 |
| Sodium lauryl sulfate | 5.5 |
| Cationic guar gum | 0.3 |
| Lactic acid | 1.0 |
| Sodium chloride | 0.2 |
| Cyclohexanone | 0.1 |
| Benzyl alcohol | 0.4 |
| Cocoyl monoethanolamide | 0.5 |
| Dimethicone (viscosity: 100,000 mPa · s) | 1.0 |
| Myristyl alcohol | 1.0 |
| Cetanol | 0.5 |
| Ethylene glycol distearate | 3.0 |
| Cocoyl benzalconium chloride | 0.5 |
| Cationic hydroxyethylcellulose | 0.3 |
| Glycerin | 1.0 |
| Sodium hydroxide | q.s. to pH 4 |
| Deionized water | Balance |

The above-described shampoo (pH:4.0, buffer capacity: 0.008) was excellent in foaming property and foam lubricity during washing, smoothness during rinsing, and hair luster and softness after drying, and was also superb in stability.

Example 10

Clear Shampoo

|  | (wt. %) |
| --- | --- |
| Sodium POE(2) lauryl ether sulfate | 10.0 |
| Cationic cellulose | 0.1 |
| Lactic acid | 0.75 |
| Sodium chloride | 1.0 |
| Lauramidopropyl betaine | 1.0 |
| Cocoyl monoethanolamide | 0.3 |
| Propylene carbonate | 0.5 |
| Glycerin | 1.0 |
| Sodium hydroxide | q.s. to pH 4 |
| Deionized water | Balance |

The above-described shampoo (pH: 4.0, buffer capacity: 0.008) was excellent in foaming property and foam lubricity during washing, smoothness during rinsing, and hair luster and softness after drying, and was also superb in stability.

The term "lower alkyl group" as used in the present invention, to define $R^1$ in component (b1), means a $C_1$ to $C_4$ alkyl group.

The molecular weight of polypropylene glycol as used herein is a number average molecular weight.

The present application claims priority to Japanese Application No. 2002-055884, filed on Mar. 1, 2002, which is hereby incorporated by reference in its entirety.

The invention claimed is:

1. A hair cleansing composition comprising the following ingredients (A) to (C):
(A) 0.5-2 wt % of glycolic acid or lactic acid and a salt thereof, wherein said salt of glycolic acid or lactic acid is a salt selected from the group consisting of a sodium salt, a potassium salt and an ammonium salt, (B) 0.5-10 wt % of a polypropylene glycol having a molecular weight of from 200 to 1,000, and (C) 8-30 wt % of a mixture of sodium POE(2) lauryl ether sulfate and sodium lauryl sulfate;

wherein said hair cleansing composition has a pH of from 1 to 4 when diluted 20-fold by weight with water, and also a buffer capacity not lower than 0.005 gram equivalent/L but lower than 0.2 gram equivalent/L, and wherein said wt % is based on the total weight of the hair cleansing composition.

2. A hair cleansing composition according to claim 1, further comprising as an ingredient (D) at least one conditioning ingredient selected from cationic polymers, cationic surfactants, silicones and oils.

3. The hair cleansing composition according to claim 1, further comprising an organic solvent represented by formula (b1):

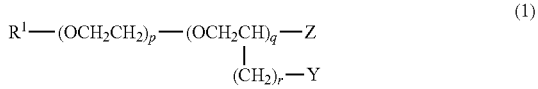

wherein $R^1$ represents a hydrogen atom or a lower alkyl group, Y and Z each independently represents a hydrogen atom or a hydroxyl group, and p, q and r each independently denotes an integer of from 0 to 5, with a proviso that, when p=q=0, both Z and $R^1$ are not a hydrogen atom.

4. The hair cleansing composition according to claim 1, further comprising an N-alkylpyrrolidone with an alkyl group having 1 to 18 carbon atoms attached to said nitrogen atom.

5. The hair cleansing composition according to claim 1, further comprising an alkylene carbonate having 1 to 4 carbon atoms.

6. The hair cleansing composition according to claim 1, further comprising a lactone or cyclic ketone represented by the following formula (2), (3) or (4):

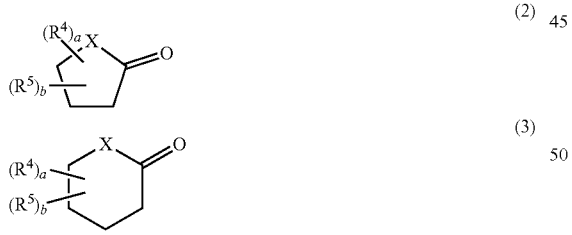

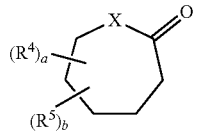

wherein X represents a methylene group or an oxygen atom, $R^4$ and $R^5$ represent different substituent groups and a and b each independently represents 0 or 1.

7. The hair cleansing composition according to claim 6, wherein said lactone or cyclic ketone is represented by formula (2).

8. The hair cleansing composition according to claim 6, wherein said lactone or cyclic ketone is represented by formula (3).

9. The hair cleansing composition according to claim 6, wherein said lactone or cyclic ketone is represented by formula (4).

10. The hair cleansing composition according to claim 1, wherein the content of (C) ranges from 8 to 22 wt % based on the total weight of the hair cleansing composition.

11. The hair cleansing composition according to claim 2, wherein the content of said at least one conditioning ingredient ranges from 0.05 wt. % to 10 wt. % based on the total weight of the hair cleansing composition.

12. A method of cleansing hair comprising the step of contacting the hair with a cleansing composition according to claim 1.

13. The hair cleansing composition according to claim 1, wherein (A) is lactic acid and a salt thereof, wherein said salt of lactic acid is a salt selected from the group consisting of a sodium salt, a potassium salt and an ammonium salt.

14. The hair cleansing composition according to claim 1, wherein said hair cleansing composition comprises the following ingredients (A) to (C):

(A) 0.5-2 wt % of lactic acid and a salt thereof, wherein said salt of lactic acid is a salt selected from the group consisting of a sodium salt, a potassium salt and an ammonium salt, (B) 0.5-10 wt % of a polypropylene glycol having a molecular weight of from 400 to 1,000, and (C) 8-30 wt % of a mixture of sodium POE(2) lauryl ether sulfate and sodium lauryl sulfate;

wherein said hair cleansing composition has a pH of from 1 to 4 when diluted 20-fold by weight with water, and also a buffer capacity not lower than 0.005 gram equivalent/L but lower than 0.2 gram equivalent/L.

15. The hair cleansing composition according to claim 1, wherein the content of (C) ranges from 10 to 22 wt % based on the total weight of the hair cleansing composition.

* * * * *